(12) United States Patent
Decitre

(10) Patent No.: US 9,000,781 B2
(45) Date of Patent: Apr. 7, 2015

(54) DEVICE FOR THE NON-DESTRUCTIVE TESTING OF AN ELECTRICALLY CONDUCTIVE STRUCTURE

(75) Inventor: Jean-Marc Decitre, Marcoussis (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 798 days.

(21) Appl. No.: 13/263,385

(22) PCT Filed: Apr. 8, 2010

(86) PCT No.: PCT/EP2010/054656
§ 371 (c)(1),
(2), (4) Date: Oct. 7, 2011

(87) PCT Pub. No.: WO2010/115963
PCT Pub. Date: Oct. 14, 2010

(65) Prior Publication Data
US 2012/0019239 A1 Jan. 26, 2012

(30) Foreign Application Priority Data

Apr. 10, 2009 (FR) ..................................... 09 52403

(51) Int. Cl.
*G01R 27/26* (2006.01)
*G01N 27/90* (2006.01)
*G01B 7/30* (2006.01)
(Continued)

(52) U.S. Cl.
CPC ................ *G01N 27/904* (2013.01); *G01B 7/30* (2013.01); *G01B 7/003* (2013.01); *A61B 5/1071* (2013.01); *A61B 2562/0261* (2013.01); *G01L 1/142* (2013.01)

(58) Field of Classification Search
CPC .......... G01B 7/30; G01B 7/003; G01L 1/142; A61B 5/1071; A61B 2562/0261
USPC .......................................... 324/658, 671, 686
See application file for complete search history.

(56) References Cited

U.S. PATENT DOCUMENTS 4,706,021 A   11/1987  Chamuel
5,047,719 A    9/1991  Johnson et al.
(Continued)

FOREIGN PATENT DOCUMENTS

FR          2 904 693         2/2008
WO    WO 2007/095971 A1      8/2007

OTHER PUBLICATIONS

International Search Report issued Jun. 28, 2010 in Application No. PCT/EP2010/054656.
(Continued)

*Primary Examiner* — Jermele M Hollington
*Assistant Examiner* — Hoang X Nguyen
(74) *Attorney, Agent, or Firm* — Oblon, McClelland, Maier & Neustadt, L.L.P.

(57) ABSTRACT

A device for non-destructive testing of an electrically conductive part including: an induction portion, a receiving portion, and a processor. The induction portion includes an inductor dissociated into n layers supplied at different frequencies f1, f2, ..., fn, wherein the receiving portion includes plural magnetic receivers supplied at different frequencies f1', f2', ..., fn' connected to one another in at least one column, each magnetic receiver being positioned under a layer, the indices n and m being integers >2, and wherein the processor makes it possible to know the magnetic field in each of the magnetic receivers of a column.

16 Claims, 6 Drawing Sheets

(51) Int. Cl.
*G01B 7/00* (2006.01)
*A61B 5/107* (2006.01)
*G01L 1/14* (2006.01)

(56) References Cited

U.S. PATENT DOCUMENTS

| | | | | |
|---|---|---|---|---|
| 6,914,427 B2* | 7/2005 | Gifford et al. | | 324/242 |
| 7,385,392 B2* | 6/2008 | Schlicker et al. | | 324/242 |
| 7,388,462 B2* | 6/2008 | Ahn et al. | | 336/200 |
| 7,489,129 B2* | 2/2009 | Meilland et al. | | 324/228 |
| 2005/0007106 A1 | 1/2005 | Goldfine et al. | | |
| 2007/0029997 A1 | 2/2007 | Goldfine et al. | | |
| 2008/0258720 A1 | 10/2008 | Goldfine et al. | | |
| 2009/0206831 A1 | 8/2009 | Fermon et al. | | |
| 2010/0109658 A1 | 5/2010 | Decitre | | |

OTHER PUBLICATIONS

U.S. Appl. No. 13/386,041, filed Jan. 20, 2012, Decitre, et al.

\* cited by examiner

DEVICE FOR THE NON-DESTRUCTIVE TESTING OF AN ELECTRICALLY CONDUCTIVE STRUCTURE

TECHNICAL FIELD

The invention relates to a device for the non-destructive testing of an electrically conductive structure.

PRIOR ART

The field of the invention is that of non-destructive testing (NDT) making it possible to detect defects, such as nicks, cracks, corrosion, etc. in conductive parts or structures.

Among all of the methods used, the electromagnetic method is particularly adapted to inspecting thin not necessarily flat conductive structures, such as aeronautical light alloy structures or steam generator tubes in nuclear power plants, wherein a lack of material can provoke leaks. This method consists in emitting, using an induction portion, an electromagnetic field in the vicinity of the structure to be inspected and in measuring, using a receiving portion (magnetic field receivers or sensors) the interference of the magnetic flow generated by the presence of a possible defect in the structure. The unit comprising the magnetic field induction portion and the receiving portion is called "probe".

The receivers can be either of the inductive type, or of the magnetic type for example AMR (Anisotropic magnetoresistance), GMR (Giant magnetoresistance), GMI (Giant magnetoimpedance), Hall effect, etc. The field of the invention relates more particularly to the second category, i.e. receivers of the magnetic type.

In order to increase the rapidity of the acquisitions, multi-element receiver units can be used, i.e. comprising multiple identical elementary receivers, in the same probe. With 1D (or one-dimensional) arrays, the displacement of the probe can be reduced to a single axis. With 2D (or two-dimensional) magnetic imagers a displacement of the probe is no longer required. In practice, there are substantial interfacing problems in order to make use of these elementary magnetic receivers, which generally have the form of quadrupoles. A highly substantial space in the probe must therefore be devoted to the interfacing, which leads to spacing the elementary receivers, and can result in the masking of the presence of a defect due to the existence of zones that are not covered by a receiver. In addition, substantial space is also taken by the electronics, which often comprise one amplifier per elementary receiver, and the means of multiplexing in the probe.

The document referenced as [1] at the end of the description describes the use of matrices or eddy current sensor arrays of the coil type, with a series connection of the emitting coils and receiving coils. The receivers of the magnetic type (GMR, etc.) are not concerned.

FIGS. 1A to 1C present a few devices of prior art that are conventionally used in non-destructive testing with an inductor 10 and a magnetic receiver 11:

The inductor 10 can be a coil, as shown in FIG. 1A, the magnetic receiver 11 being located at a few millimeters or about ten millimeters from this coil, the arrow 12 indicating the direction of the current.

The inductor 10 can be a "layer" which makes it possible, under the wires, to generate a local homogeneous distribution of the magnetic field, as shown in FIG. 1B, the magnetic receiver 11 being arranged under these wires, the arrows 12 indicating the direction of the current.

The inductor 10 can be a double layer, as shown in FIG. 1C, the magnetic receiver 11 being arranged at the centre of the layer, the arrows 12 indicating the direction of the current.

The field of the invention is more particularly that of inductors of the "layer" type, such as shown in FIG. 1B or 1C, and magnetic receivers of the GMR type, or also of the GMI, AMR, TMR (tunnel magnetoresistance) type, etc. Magnetic detection can be used as a mixing function, as described in document [2]. There is then a supplying of the layer at a frequency f, this frequency being generally fixed according to the material studied and characteristics of the defect to be detected. The supplying, for example in current, of the magnetic detector can be either direct, or alternating at a frequency f'. If the supplying is direct, the demodulation of the complex signal at the terminals of the magnetic detector is carried out at a frequency f. If it is alternating, two rays appear in the signal, one at the frequency f−f' and the other at the frequency f+f' and a demodulation at f−f' or f+f' determines the amplitude of the complex voltage at this frequency. After demodulation, the amplitude is proportional to the current which passes through the detector and to the magnetic field wherein it is located.

In the case of a multi-element receiver unit, as shown in FIGS. 2A and 2B, the elementary receivers 20 are conventionally positioned next to one another and are independent. The inductor layer, represented by a solid rectangle 21, covers all of these elementary receivers. The arrows 22 indicate the direction of the current. In the case of FIG. 2A, in order to cover a substantial surface, the entire receiver is displaced according to the axis Y. In the case of FIG. 2B, the probe (inductor+receivers) can be used without movement and carry out a static mapping of the magnetic field radiated by the defects in a structure.

The interfacing of the devices of prior art is complex due to the use of at least one connection per element. As such, a magnetic detection of the GMR type conventionally requires two supply wires and two differential measurement wires. The latter are connected to differential amplifiers. Then analog multiplexer/demultiplexers are indispensable in order to reduce the number of connections between the probe and the instrumentation. The latter comprises, in a conventional manner, synchronous demodulators in order to make use of the signals as non-destructive testing via eddy currents, and in order to obtain the complex amplitude of the ray at the demodulation frequency.

The invention has for object to resolve these technical problems by proposing a device for testing comprising a multi-element receiver unit in the form of an array or matrix of elementary magnetic receivers, which makes it possible to minimise the interfacing and the electronics by supplying the elementary magnetic receivers in series or in parallel in order to increase their density and minimise the zones of the structure to be tested that are not covered by an elementary magnetic receiver.

DESCRIPTION OF THE INVENTION

The invention relates to a device for the non-destructive testing of an electrically conductive part comprising:
an induction portion, and
a receiving portion,
processing means,
characterised in that the induction portion comprises an inductor dissociated into n elementary inductors of the layer type supplied at different frequencies $f_1, f_2, \ldots, f_n$, and in that the receiving portion comprises n' magnetic receivers distributed over m columns, each column comprising at most n receivers, the magnetic receivers being connected to one another over each column, the m columns of receivers being supplied by electrical signals $v_1', v_2', \ldots, v_m'$, of frequencies $f_1', f_2', \ldots, f_m'$ zero or non-zero, each magnetic receiver being arranged under an elementary inductor, m magnetic receivers being positioned under each elementary inductor, the indices n, n' and m being positive integers such that $n \geq 2$, $1 < n' \leq n*m$ and $m \geq 1$ and in that the processing means make it possible to know the magnetic field in each of the magnetic receivers of a column, and in that each magnetic receiver is used as a demodulator.

Each elementary inductor can be a layer comprising a conductive wire, or several conductive strands in series, or several conductive strands in parallel.

Advantageously, the magnetic receivers are connected in series.

In a first embodiment, each column i of receivers is supplied in current, the voltage measured at the terminals of a column being the sum of at most 2n sinusoidal elementary voltages, at the frequencies $f_1 \pm f'i, f_2 \pm f'_i, \ldots$ and $f_n \pm f'_i$ and of the means demodulating à $f_1 + f'_i, f_2 + f'_i, \ldots, f_n + f'_i$ or $f_1 - f'_i, f_2 - f'_i, \ldots, f_n - f'_i$.

In a second embodiment, each column of receivers is supplied in voltage, the current passing through a column i being the sum of at most 2n sinusoidal elementary currents, at frequencies $f_1 \pm f'i_i, f_2 \pm f'_i, \ldots$ and $f_n \pm f'_i$ and of the means of demodulating à $f_1 + f'_i, f_2 + f'_i, \ldots, f_n + f'_i$, or $f_1 - f'_i, f_2 - f'_i, \ldots, f_n - f'_i$.

In a third embodiment, each column i of receivers constitutes a branch of a Wheatstone resistive bridge, supplied by an alternating voltage and of which the differential imbalance voltage is measured at frequencies $f_1 \pm f'_i, f_2 \pm f'_i, \ldots, f_n \pm f'_i$ and of the means of demodulating at $f_1 + f'_i, f_2 + f'_i, \ldots, f_n + f'_i$ or $f_1 - f'_i, f_2 - f'_i, \ldots, f_n - f'_i$.

Advantageously, the magnetic receivers are directed according to the axis X of sensitivity, the main direction of the currents of these elementary receivers being directed according to the axis Y.

In an example embodiment, the device of the invention comprises a matrix of m×n magnetic receivers (i.e. n'=n: each column i contains as many receivers as there are elementary inductors), the frequencies $f_1, f_2, \ldots, f_n$ are respectively equal to frequencies $f+\Delta f, f+2\Delta f, \ldots, f+n\Delta f$ and the frequencies $f'_1, f'_2, \ldots, f'_n$ are all equal to the frequency f, the frequency f can be about 1 MHz and the frequency $\Delta f$ about 10 KHz.

According to another example embodiment, the supplying of the receivers is carried out directly ($f'_1=f'_2=\ldots=f'_n=0$) and the frequencies $f_1, f_2, \ldots, f_n$ are respectively equal to frequencies $f+\Delta f, f+2\Delta f, \ldots, f+n\Delta f$. The frequency f can be about 1 MHz and the frequency $\Delta f$ about 20 KHz.

Advantageously, the device of the invention comprises a support whereon are positioned the inductors and the magnetic receivers, which can be a flexible multi-layer printed circuit. These magnetic receivers can be direct wired receivers. The induction portion can include several layers distributed over at least one layer of a multi-layer substrate.

Advantageously, the magnetic receivers are receivers of the GMR type.

The device of the invention has many advantages, and in particular:

- a minimisation of the interfacing and an increase in the density of the elementary receivers,
- a minimisation of the processing electronics within the device,
- a simplification of the implementation of the magnetic receiver unit,
- a possibility of carrying out 2D imagers.

The device of the invention can be in particular used for multi-element applications for non-destructive testing via eddy currents, and more particularly for applications aimed at detecting small defects on the surface of a structure.

DETAILED DESCRIPTION OF PARTICULAR EMBODIMENTS

Figure 3:
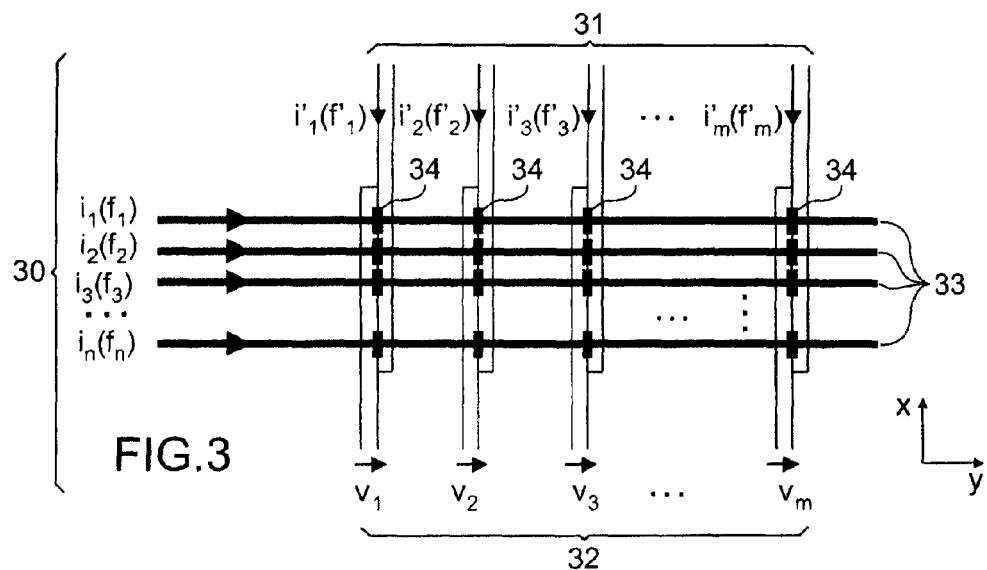
FIG. 3 shows the device of the invention.

The device of the invention, as shown in FIG. 3, comprises:
- an induction portion comprising an inductor dissociated into n elementary inductors 33 supplied at different frequencies f1, f2, ..., fn,
- a receiving portion comprising n' magnetic receivers 34 distributed over m columns, each column comprising at most n magnetic receivers 34, these magnetic receivers being connected to one another over each column, the m columns of receivers being supplied by electrical signals v1', v2', ..., vm', of frequencies f1', f2', ..., fm', zero or non-zero, each magnetic receiver 34 being arranged under an elementary inductor, the indices n, n' and m being positive integers such that $n \geq 2$, $1 < n' \leq n*m$ and $m \geq 1$
- processing means making it possible to know the magnetic field in each of the magnetic receivers 34 of a column.

There is an inductor supply 30, a supplying 31 of the magnetic receivers 34 and of the receiving channels 32.

The electrical signals v1', v2', ..., vm' can be either direct currents or voltages, or alternating currents or voltages of respective frequencies f1', f2', ..., fm'. In the remainder of this document, in order to simplify the cases, it shall be considered the most general case where the voltages v1', v2', ..., vm' are either sinusoidal of frequencies f1', f2', ..., fm', or are direct by considering in this case f1'=f2'=...=fm'=0.

Figure 1A:
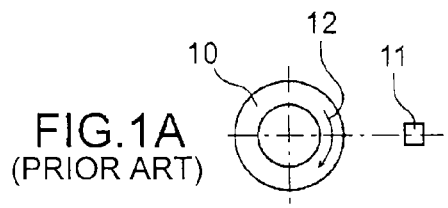
FIGS. 1A, 1B, 1C and 1D and 2A and 2B show inducer/receiver devices of prior art.
Figure 1B:
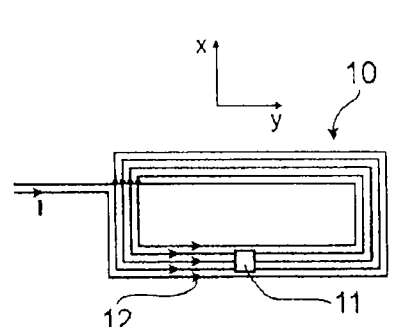
Figure 1C:
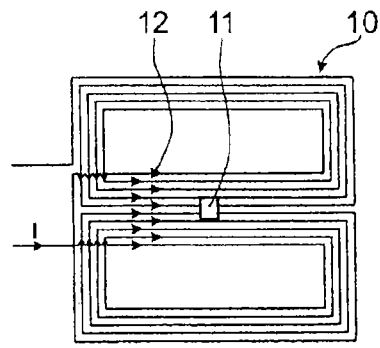
Figure 1D:
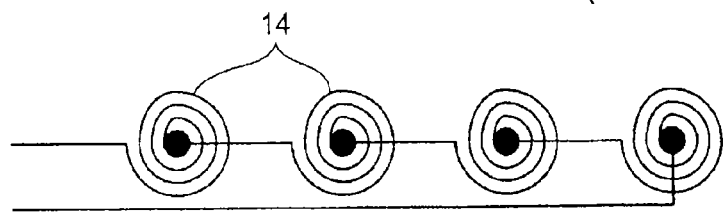
Figure 2A:
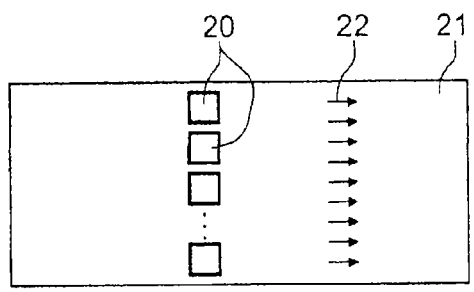
Figure 2B:
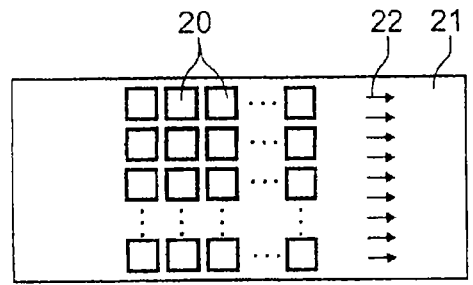

Each elementary inductor 33 can be a layer comprising a conductive wire, or several conductive strands in series as shown in FIGS. 1B and 1C, or several conductive strands in parallel. It is possible for the strands not to be straight. They can be constituted of small elementary layers supplied by the same current or coils 14, such as shown in FIG. 1D.

Each magnetic receiver 34 is used as a demodulator. As such, for example, the voltage v1 measured at the terminals of the first column of magnetic receivers 34 placed in series is the sum of 2n sinusoidal elementary voltages, at f1±f'1, f2±f'1, . . . , and fn±f'1. Demodulations of v1 at f1–f'1, f2–f'1, . . . , and fn–f'1 or f1+f'1, f2+f'1, . . . , and fn+f'1 make it possible to derive the complex amplitude of the component of v1 at each of these frequencies and subsequently to derive the magnetic field present in each of the measuring points, or receivers, of the column. Multiplexers are not required.

The supplying 31 of the columns of magnetic receivers 34 in series can be a supplying in voltage, the current passing through these receivers then being the measured signal.

In a first embodiment, each column i comprising n'i receivers is supplied in current at the frequency f'i, the voltage measured at the terminals of this column i being the sum of 2n'i elementary voltages (n'i in the case where f'i=0), at most at the frequencies f1±f'i, f2±f'i, . . . and fn±f'i (with the amplitude at some of these frequencies being zero or very low in the absence of a receiver under an elementary inductor of the column).

In a second embodiment, each column i is supplied in voltage at the frequency f'i, the current passing through a column i being the sum of 2n'i elementary currents, at most at the frequencies f1±f'i, f2±f'i, . . . , and fn±f'i.

In a third embodiment, each column i comprising n'i receivers is inserted into a branch of a Wheatstone bridge. The three impedances of the bridge are for example resistances, each with a value close to the resistance of the total column of magnetic receivers. Each bridge i is supplied at the frequency f'i. The differential imbalance voltage, measured at the terminals of the intermediary branches of the bridge, is the sum of 2n'i elementary voltages, at most at the frequencies f1±f'i, f2±f'i, . . . and fn±f'i.

In any case, the demodulation is carried out either at the frequencies f1–f'i, f2–f'i, . . . and fn–f'i or at the frequencies f1+f'i, f2+f'i, . . . and fn+f'i, in order to determine the local magnetic field on each of the receivers. In the particular case wherein the supplying of the column of the receiver is direct, the demodulation must be carried out at the frequencies f1, f2, . . . and fn since f1'=f2'= . . . =fm'=0.

It is possible by correctly choosing the frequencies f1, . . . , fn, and f'1, . . . , f'm, to sum the reception voltages v1, v2, . . . , vm into a single signal by using means of amplification, and demodulate this single signal using means of demodulating at the n×m frequency differences fi–f'j. A single receiving cable is then required between the device of the invention (probe) and the means of demodulating. With the device of the invention, the number of connections is therefore limited.

Figure 4A:
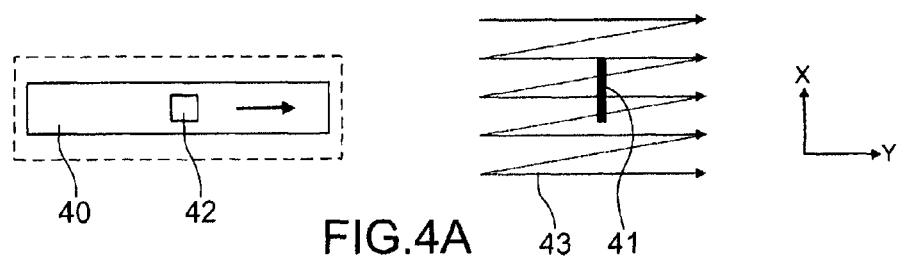
FIGS. 4B to 4D show the appearance of mappings of magnetic field obtained according to the orientation of the magnetic receiver during the displacement of an example embodiment of the device of the invention shown in FIG. 4A.
Figure 4B:
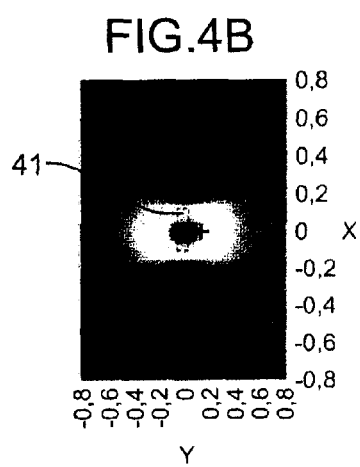
Figure 4C:
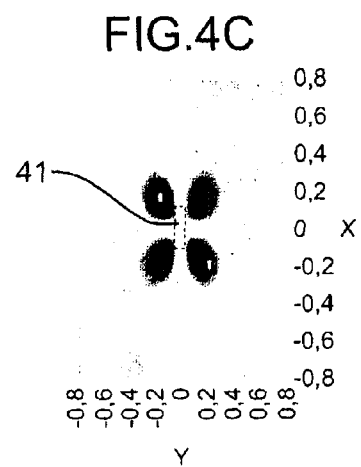
Figure 4D:
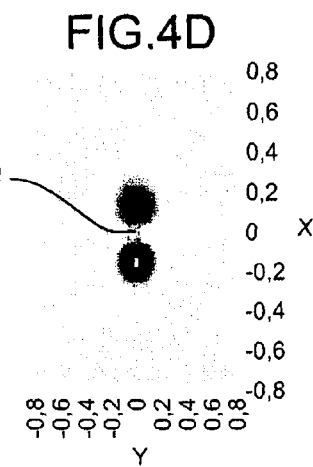

The magnetic receivers 34 have an axis of sensitivity. They can be preferentially directed according to one of three axes X, Y or Z. FIGS. 4B to 4D provide the appearance of the mappings of magnetic fields obtained during the displacement (sweeping) 43 according to the axes X and Y of an example embodiment of the device of the invention, shown in FIG. 4A, which comprises an elementary inductor 40, directed according to the axis Y above a nick 41 in the structure to be tested, and a magnetic receiver 42. This magnetic receiver 42 can be directed according to the axis X, which makes it possible to obtain the mapping shown in FIG. 4B, according to the axis Y which makes it possible to obtain the mapping shown in FIG. 4C, or according to the axis Z which makes it possible to obtain the mapping shown in FIG. 4D. A globally single-pole signal is obtained in the case shown in FIG. 4B (axis X) by neglecting the small secondary lobes, on either side, of amplitude that is clearly less substantial than the central lobe, a quadrupole signal in the case shown in FIG. 4C (axis Y) and a bipolar signal in the case shown in FIG. 4D (axis Z).

Figure 5:
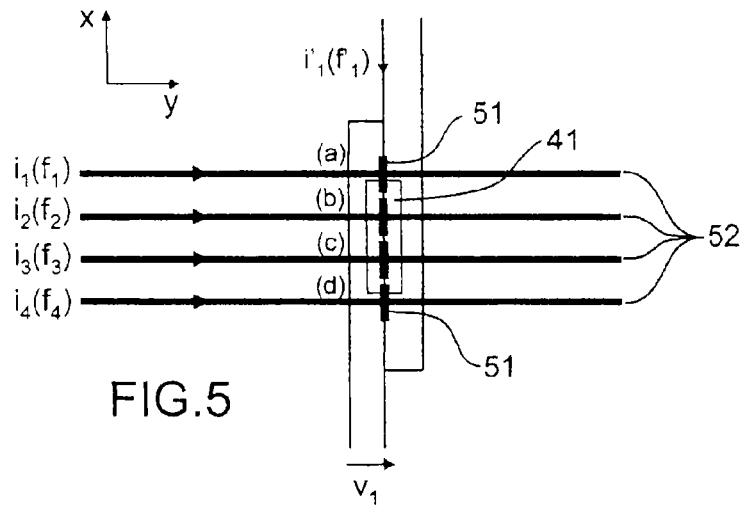
FIG. 5 shows an example embodiment of the device of the invention.

FIG. 5 shows an example embodiment of the device of the invention, wherein the defect (nick 41) is located at the centre of an inductor comprising four elementary inductors 52, and four corresponding magnetic receivers 51, denoted respectively a, b, c and d. The signal v1 due to the nick 41 resulting from the placing in series of the four magnetic receivers 51 is theoretically zero in the case of an orientation of the receiver according to the axis Y or the axis Z: for reasons of symmetry, the contributions of the magnetic receivers b and c are identical but of opposite signs, likewise for the magnetic receivers a and d. Such configurations can therefore result in non-detections of defects, which is not the case with an orientation according to the axis X of the magnetic receiver, due to the parity, according to the columns, of the mapping shown in FIG. 4B. The configuration for measuring according to the axis X is therefore more advantageous within the framework of the device of the invention.

Figure 6:
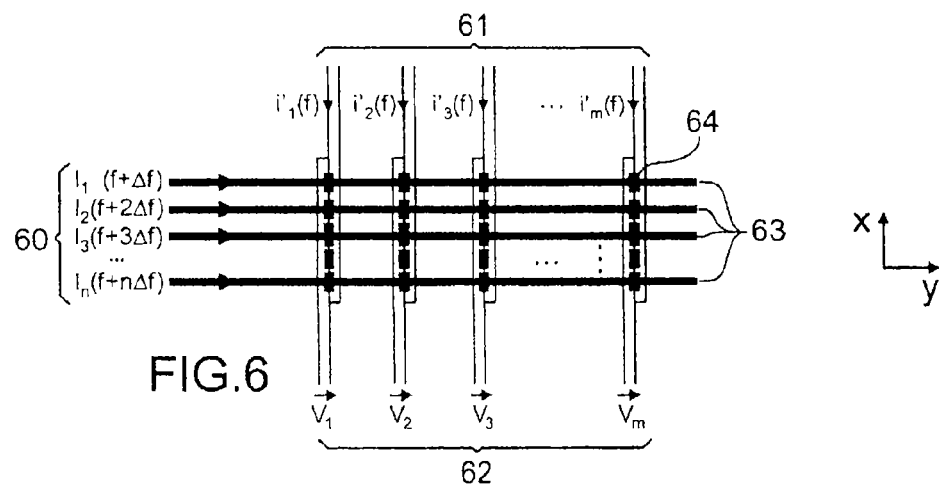
FIGS. 6 to 9B show another example embodiment of the device of the invention, FIG. 9B being a cross-section view of FIG. 9A according to the plane A-A.

An example of a simplified embodiment in terms of the choice of frequencies is shown in FIG. 6 with a matrix of m×n magnetic receivers, with the induction supply 60 of the elementary inductors 63 at frequencies f+$\Delta$f, f+2$\Delta$f, . . . , f+n$\Delta$f, the supplying 61 of the receivers 64 at the frequency f and the receiving channels 62 making it possible to obtain sums of signals of frequencies $\Delta$f, 2$\Delta$f, 3$\Delta$f, . . . , n$\Delta$f. For each of the columns of magnetic receivers 64, the demodulation is as such carried out at $\Delta$f, 2$\Delta$f, . . . , n$\Delta$f.

Figure 7:
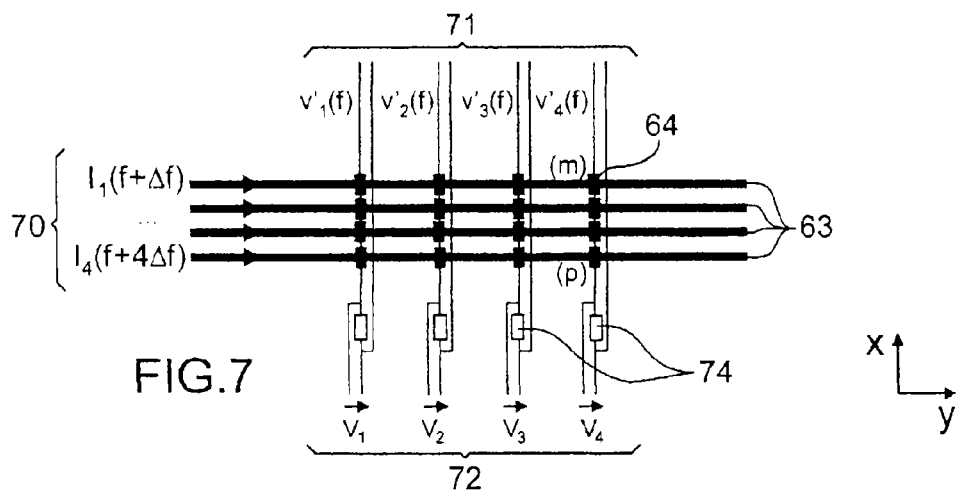

FIG. 7 includes the simplified example embodiment of FIG. 6 with a matrix of 4×4 magnetic receivers 64, all directed according to the axis X. The test frequency f is about 1 MHz and the frequency $\Delta$f about 10 kHz. The used magnetic receivers 64 are plunged into a direct magnetic field of polarisation directed according to their axis of sensitivity so that they can operate in their domain of linearity. This polarisation is carried out by conductive wires, supplied with an adjustable direct current voltage, passing under the magnetic receivers. In FIG. 7 are also shown the inductor supply 70 at the frequencies f+$\Delta$f, . . . , f+4$\Delta$f, the supply 71 of the magnetic receivers 64 at the frequency f and the receiving channels 72 (sum of the signals at the frequencies $\Delta$f, 2$\Delta$f, 3$\Delta$f and 4$\Delta$f). The reference 74 shows resistances of a low value of the measurement of the image of the current.

Figure 8:
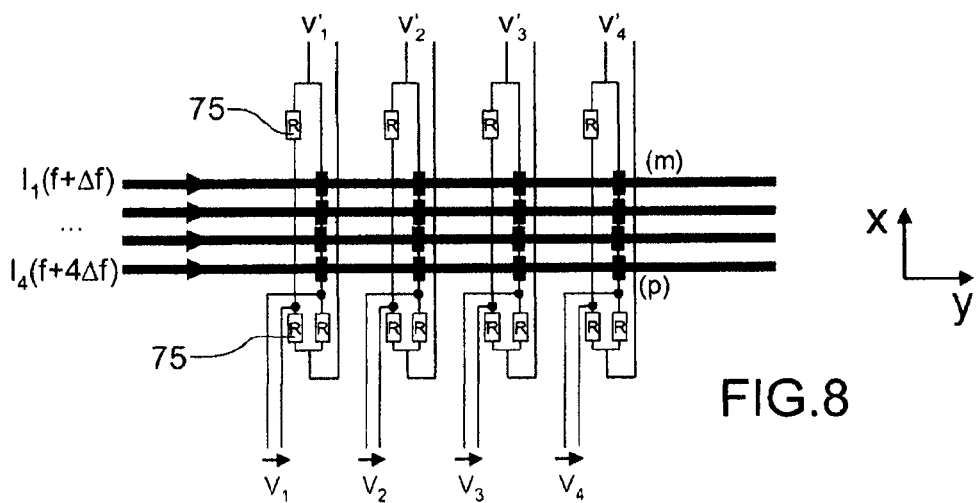

FIG. 8 includes the example of the simplified embodiment of FIG. 7 in the third embodiment, each column comprising 4 receivers being inserted into a branch of a Wheatstone bridge (resistances 75).

The support used for the magnetic receivers 64 and the elementary inductors 63, which can be positioned on either side of the latter, is a flexible printed circuit, for example a "flex" printed circuit made of epoxy of 400 μm in thickness. Such a circuit makes it possible for the device of the invention to mould complex forms. Each of the columns of magnetic receivers is supplied by an alternating voltage v'1, v'2, v'3 or v'4 and the resistances of a low value 74 inserted in series with the magnetic receivers 64 each make it possible to measure a image voltage of the current in the magnetic receivers 64. This voltage comprises in particular rays at the frequencies $\Delta$f, 2$\Delta$f, 3$\Delta$f and 4$\Delta$f, which, after demodulation at these frequencies, make it possible to detect the possible presence of a nick in the structure or in the part to be tested.

Figure 9A:
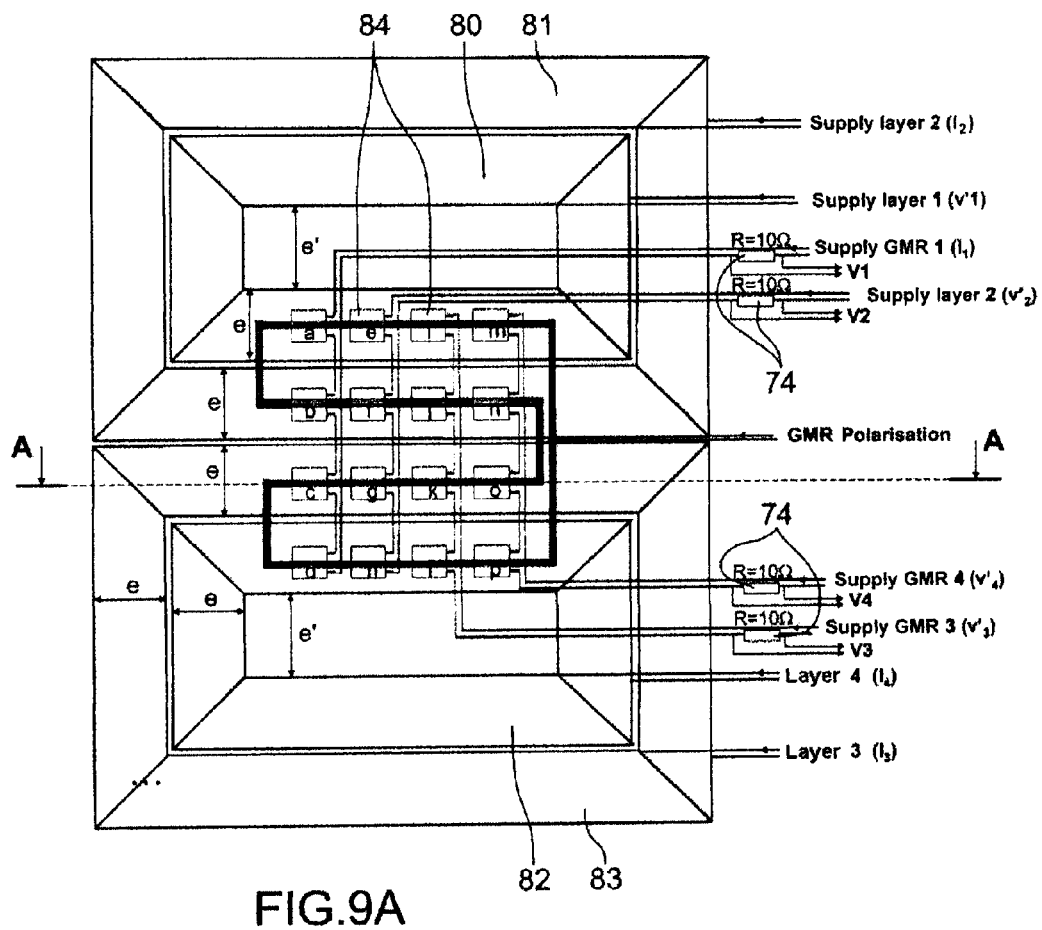
Figure 9B:
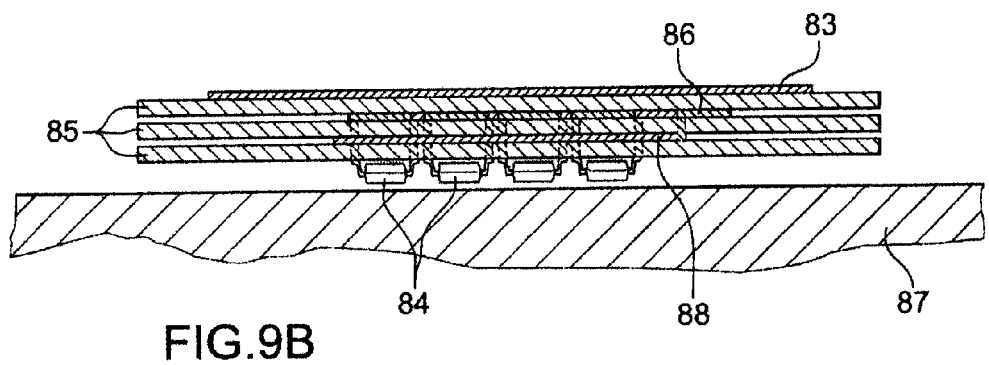

FIGS. 9A and 9B show the example embodiment of FIG. 7, by showing four elementary inductors 80, 81, 82 and 83, and 4×4 magnetic receivers 84, for example of the GMR type, referenced respectively by the letters a to p, with their respective supplies. The receivers a, e, i, m are as such positioned under the layer 80, the receivers b, f, j, n under the elementary inductor 81, the receivers c, g, k, o under the elementary inductor 82 and the receivers d, h, l, p under the elementary inductor 84. The widths e of the shown elementary inductors can be, for example, equal to 7 mm and the width e' of the internal opening of the elementary inductors 80 and 82 equal to 8 mm.

As shown in FIG. 9B, the elementary inductors 80, 81, 82 and 83, on the one hand, and the magnetic receivers 84, on the other hand, are positioned on either side of a support 85, constituted here by a four-layer printed circuit. The interfacing 86, and the polarising coil 88 being arranged between these layers. The reference 87 shows the part to be tested.

Figure 10A:
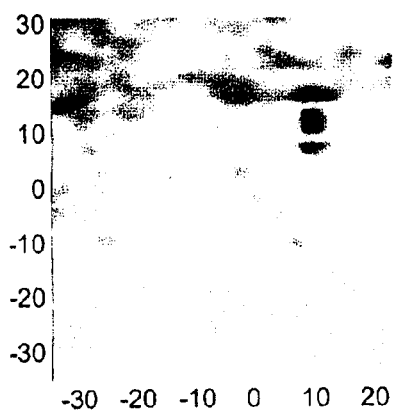
FIGS. 10A and 10B show experimental results obtained with the example embodiment of the device of the invention such as shown in FIGS. 9A and 9B.
Figure 10B:
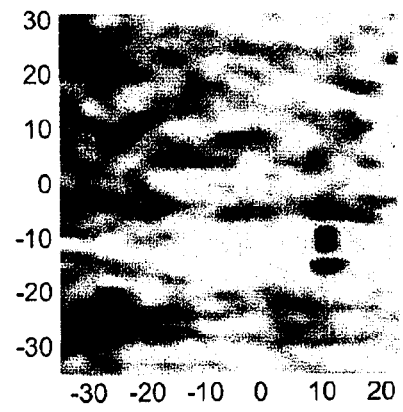

The device of the invention shown as such in FIGS. 9A and 9B can be tested by sweeping over a flat part comprising an electro-eroded defect of 10 mm in length made on the surface. FIGS. 10A and 10B show the signal obtained, using magnetic receivers referenced n and p, after demodulation of the voltage v4 at the frequencies Δf and 4Δf. The two magnetic receivers m and p make it possible to correctly detect this defect in a totally independent manner and without crosstalk.

Figure 11:
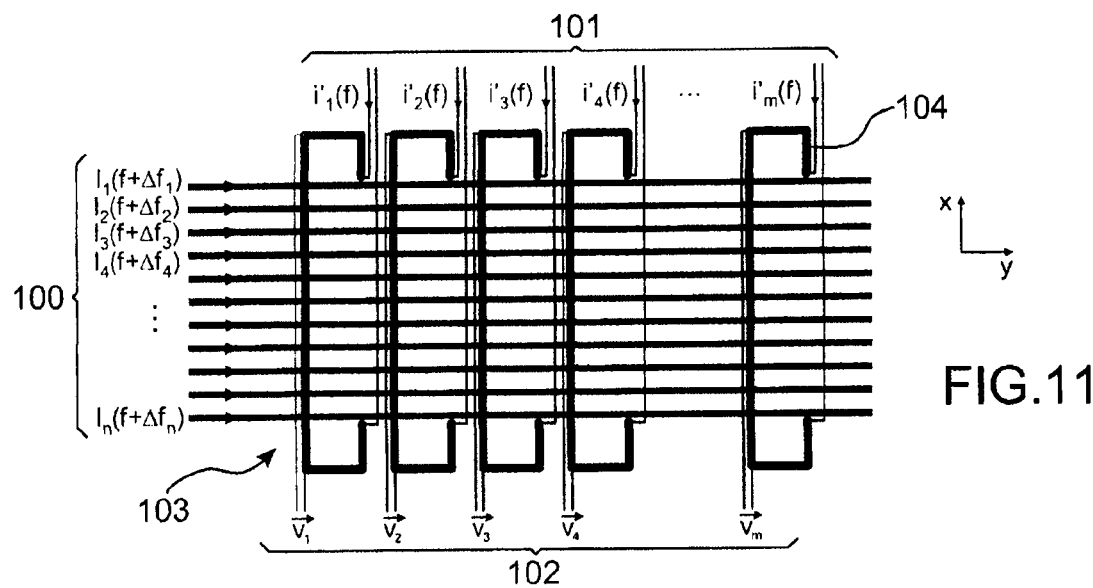
FIGS. 11 and 12A to 12F show other example embodiments of the device of the invention.

A multi-element magnetic receiver unit can be carried out with magnetic receivers in the shape of a "C" ("yoke") 103, as shown in FIG. 11, of which the space between two neighbouring magnetic receiver elements 104, is approximately 100 μm. The connection requirements prevent the carrying out of a 2D matrix in light of the space required for the interconnection contacts. But it is possible to retain only two exterior contacts for each elementary receiver, as shown in FIG. 11, by using, as previously, a circuit for demodulating and making use of the signals coming from the various magnetic receiver elements. FIG. 11 shows the inductor supply 100, the receiver supply 101, and the receiving channels 102 (sum of the voltages at Δf1, Δf2, ..., Δfn). As such, the elementary magnetic receivers 104 are no longer discrete but continuous. Such a receiver unit has other advantages, and in particular:

Eddy current probes can be used with a high density of sensors.
  The stray capacities brought via the contacts are suppressed, which is particularly advantageous at frequencies exceeding a few hundred kHz.
  The carrying out and the connecting of the magnetic receiver unit is then largely simplified.
  The near sensor low noise amplifier electronics can be minimised if required, by using one amplifier per column instead of one per element.
  The magnetic receiver unit can be very long, for example several centimeters.

Figure 12A:
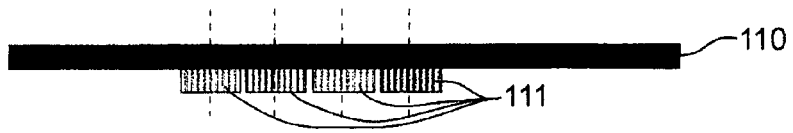
Figure 12B:
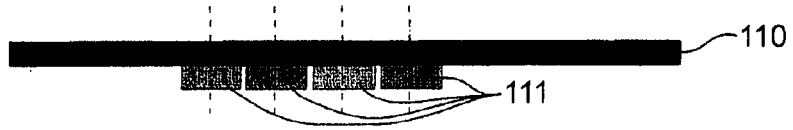
Figure 12C:
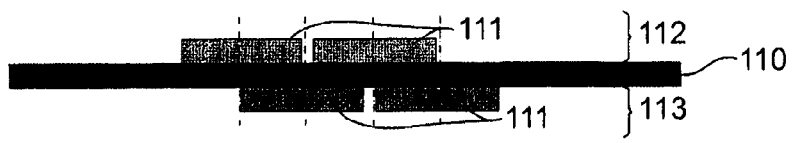
Figure 12D:
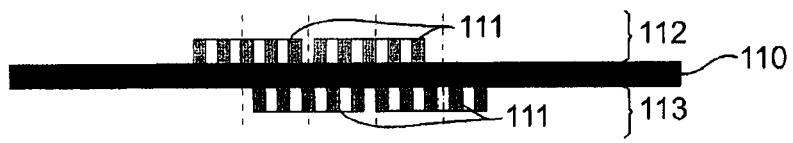
Figure 12E:
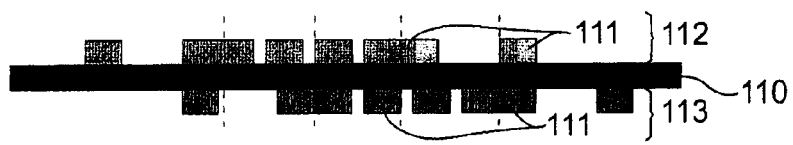
Figure 12F:
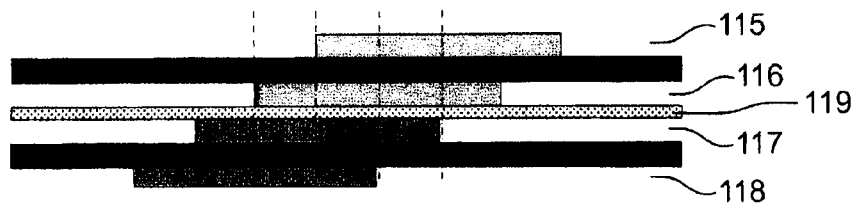

In the device of the invention, the elementary inductors 111 constituting the induction portion can be carried out either with a single solid conductor (wire), or with various conductive strands placed in series or in parallel. As shown on FIGS. 12A to 12F, the strands of the same elementary inductor 111 can be distributed over various layers of a multi-layer substrate 110 (printed circuit, kapton, etc.). The successive strands can also be partially superimposed by using a multi-layer substrate, or nested. FIGS. 12A to 12F show various example embodiments for four elementary inductors 111 arranged on a layer as shown in FIGS. 12A and 12B, over two layers 112 and 113 as shown in FIGS. 12C to 12E or over four layers 115, 116, 117, 118 as shown in FIG. 12F, with layer 119 being an insulation layer.

In alternative embodiments of the device of the invention, the following can be used:
  magnetic receivers in parallel instead of being placed in series,
  elementary inductors in the form of large circular coils or placing small coils in series,
  a magnetic tape above the elementary inductors in order to increase the inductor field,
  a staggered arrangement of the magnetic receivers,
  a flexible substrate (kapton or flexible printed circuit),
  the use of magnetic receivers of the GMR type or of the quadrupole type: AMR, TMR, GMI, etc.,
  an operation with integrated magnetic receivers mounted in a bridge,
  the use of receivers with magnetic elements in order to concentrate the flow in the magnetic receiving according to the axis of sensitivity.

REFERENCES

[1] FR 2 904 693
[2] WO 2007/095971

The invention claimed is:

1. A device for non-destructive testing of an electrically conductive part comprising:
  an induction portion;
  a receiving portion; and
  processing means;
  wherein the induction portion comprises an inductor dissociated into n elementary inductors of layer type supplied at different frequencies $f_1, f_2, \ldots, f_n$;
  wherein the receiving portion comprises n' magnetic receivers distributed over m columns, each column comprising at most n receivers, the magnetic receivers being connected to one another over each column, the m columns of receivers being supplied by electrical signals $v_1', v_2', \ldots, v_m'$, of frequencies $f_1', f_2', \ldots, f_m'$, zero or non-zero, each magnetic receiver being arranged under an elementary inductor, m magnetic receivers being positioned under each elementary inductor, the indices n, n' and m being positive integers such that n>=2, 1<n'<=n*m and m>1,
  wherein the processing means comprises, for each column of receivers of row i with 1≤i≤m, means of measuring the signal at terminals of this column of receivers followed by means of demodulating this signal at the frequencies f1+f'i, f2+f'i - - - fn+f'i or f1−f'i, f2−f'i - - - fn−f'i and means of calculating the magnetic field in each of the receivers of this column, and
  wherein the magnetic receivers are directed according to an axis of sensitivity, a main direction of currents of these elementary receivers being directed according to a perpendicular axis.

2. A device according to claim 1, wherein each elementary inductor is a layer comprising a conductive wire, or plural conductive strands in series, or plural conductive strands in parallel.

3. A device according to claim 1, wherein the magnetic receivers are connected in series.

4. A device according to claim 1, wherein each column i of receivers is supplied in current, voltage measured at the terminals of a column being the sum of at most 2n sinusoidal elementary voltages, at frequencies $f_1 \pm f'_i, f_2 \pm f'_i, \ldots$ and $f_n \pm f'_i$ and of means of demodulating at $f_1+f'_i, f_2+f'_i, \ldots, f_n+f'_i$ or $f_1-f'_i, f_2-f'_i, \ldots, f_n-f'_i$.

5. A device according to claim 1, wherein each column i of receivers is supplied in voltage, current passing through a column being the sum of at most 2n sinusoidal elementary currents, at frequencies $f_1 \pm f'i, f_2 \pm f'_1, \ldots$ and $f_n \pm f'_i$ and of the means of demodulating at $f_1+f'_i, f_2+f'_i, \ldots, f_n+f'_i$ or $f_1-f'_i, f_2-f'_i, \ldots, f_n-f'_i$.

6. A device according to claim 1, wherein each column i of receivers constitutes a branch of a Wheatstone resistive bridge, supplied by a signal at frequency $f'_i$ and of which differential imbalance voltage is measured at frequencies $f_1 \pm f'_i, f_2 \pm f'_i, \ldots$ and $f_n \pm f'_i$ and of the means of demodulating at $f_1+f'_i, f_2+f'_i, \ldots, f_n+f'_i$ or $f_1-f'_i, f_2-f'_i, \ldots, f_n-f'_i$.

7. A device according to claim 1, comprising a matrix of m×n magnetic receivers and wherein the frequencies $f_1, f_2, \ldots, f_n$ are respectively equal to frequencies $f+\Delta f, f+2\Delta f, \ldots, f+n\Delta f$ and wherein the frequencies $f'_1, f'_2, \ldots, f'_m$ are all equal to the frequency f.

8. A device according to claim 1, comprising a matrix of m×n magnetic receivers and wherein the frequencies $f_1, f_2, \ldots, f_n$ are respectively equal to frequencies $f+\Delta f, f+2\Delta f, \ldots, f+n\Delta f$ and wherein the signals $v'_1, v'_2, \ldots, v'_m$ are direct.

9. A device according to claim 8, wherein the frequency f is about 1 MHz and the frequency ΔF about 10 KHz.

10. A device according to claim 1, wherein the elementary inductors and the magnetic receivers are positioned on a support.

11. A device according to claim 10, wherein the support is a flexible printed circuit.

12. A device according to claim 10, wherein the support is a multi-layer printed circuit.

13. A device according to claim 1, comprising direct wired magnetic receivers.

14. A device according to claim 1, wherein the induction portion comprises plural layers distributed over at least one layer of a multi-layer substrate.

15. A device according to claim 1, wherein the magnetic receivers are receivers of GMR type.

16. A device according to claim 1, wherein the inductor is coupled to a magnetic tape.

* * * * *